(12) United States Patent
Gofman et al.

(10) Patent No.: US 6,241,520 B1
(45) Date of Patent: Jun. 5, 2001

(54) ULTRASONIC SCALER WITH ADAPTIVE AMPLITUDE

(75) Inventors: Igor Y. Gofman, Croton-on-Hudson; Steven Abdelgader, Thiells; Joseph G. Colombo, Lodi, all of NY (US)

(73) Assignee: Coltene/Whaledent, Mahwah, NJ (US)

( * ) Notice: Subject to any disclaimer, the term of this patent is extended or adjusted under 35 U.S.C. 154(b) by 0 days.

(21) Appl. No.: 09/306,624

(22) Filed: May 6, 1999

(51) Int. Cl.⁷ .............................. A61C 1/07; A61C 3/03; A61C 3/08
(52) U.S. Cl. ......................................................... 433/119
(58) Field of Search ............................... 433/86, 118, 119

(56) References Cited

U.S. PATENT DOCUMENTS

| | | |
|---|---|---|
| 5,059,122 * | 10/1991 | Hetzel ................................ 433/118 |
| 5,451,161 | 9/1995 | Sharp . |
| 5,730,594 | 3/1998 | Sharp . |
| 6,019,775 * | 2/2000 | Sakurai ............................... 433/119 |

FOREIGN PATENT DOCUMENTS 31 36 028   3/1983 (DE) .

* cited by examiner

Primary Examiner—Nicholas D. Lucchesi
(74) Attorney, Agent, or Firm—Helfgott & Karas, P.C.

(57) ABSTRACT

An automatic drive circuit for an ultrasonic probe, such as a dental scaler insert, is operative with a probe which includes a magnetostrictive unit and a vibratory element to be set into vibration by the magnetostrictive unit upon energization of the magnetostrictive unit with an alternating magnetic field. An energizing coil is enclosed within a handle having a compartment for receiving the probe. The coil is located within the handle adjacent to the probe-receiving compartment for applying the alternating magnetic field to the magnetostrictive unit upon insertion of the probe into the handle and upon energizing the coil by the drive circuit. An oscillator of the drive circuit is coupled to the coil for applying an oscillatory current to the coil. The drive circuit includes a frequency sensor for sensing a frequency of the oscillatory current, the sensor outputting a signal designating a magnitude of the frequency. A further component of the drive circuit establishes a value of amplitude of the alternating current in response to the sensed value of the frequency. The circuitry relies on the inductance introduced via the magnetostrictive unit to the coil for automatically establishing the value of oscillation frequency commanded by the probe.

18 Claims, 3 Drawing Sheets

ULTRASONIC SCALER WITH ADAPTIVE AMPLITUDE

BACKGROUND OF THE INVENTION

This invention relates to a circuit for driving an ultrasonic scaling probe suitable for use in dentistry, primarily for removal of plaque, cements, composites, etc. The invention utilizes an automatically tuned drive circuit.

Electronic circuits have been employed for driving ultrasonic dental scalers. By way of example. Sharp (U.S. Pat. No. 5,451,161) discloses such a circuit operative with a scaler insert for a hand piece of a dental scaler unit. The circuitry produces an oscillation at a frequency established by the insert, and employs the energizer coil of the hand piece as a feedback coil for operation of the circuit. Different scaler inserts are operative at different frequencies and, accordingly, the circuitry includes a manual switching of capacitors to adjust oscillation frequency.

As a further example, German patent 3,136,028 also employs the energizer coil as a part of a feedback portion of an oscillator circuit. Multiple frequencies of oscillation are obtained by use of a variable resistor and capacitor as a part of the oscillator circuit. Also, Sharp (U.S. Pat. No. 5,730,594) discloses a switch which operatively switches between an automatic tuning and a manual tuning of an oscillator circuit for the driving of the dental scaler.

The foregoing circuits suffer from the disadvantage of requiring manual intervention in the operation of the drive circuit to establish a specific frequency of operation as may be required by the specific choice of a scaler insert for the hand piece. In addition, the foregoing circuits, while providing for the capacity of enabling different frequencies of operation, do not have a facility for automatically establishing a desired amplitude of drive signal for the scaler insert as a function of the operating frequency, or even maintaining a constant amplitude throughout an operating frequency range of the drive circuit.

SUMMARY OF THE INVENTION

The aforementioned problems are overcome and other advantages are provided by an automatic drive circuit for an ultrasonic probe wherein the probe includes a magnetostrictive unit and a vibratory element to be set into vibration by the magnetostrictive unit upon energization of the magnetostrictive unit with an alternating magnetic field. An energizing coil is enclosed within a handle, the handle having a compartment for receiving the probe. The coil is located within the handle adjacent the probe-receiving compartment for applying the alternating magnetic field to the magnetostrictive unit upon insertion of the probe into the handle and upon an energizing of the coil by the drive circuit.

In accordance with the invention, an oscillator of the drive circuit is coupled to the handle coil for applying an oscillatory current to the magnetostrictive element. The drive circuit includes a frequency detector for sensing the frequency of the magnetostrictive element. The detector's output signal designates a magnitude of the frequency. A component of the drive circuit establishes a value of amplitude of the alternating current in response to the sensed value of the frequency. The automatic circuit relies on the current introduced via the magnetostrictive element to a tapped coil for automatically establishing the value of oscillation frequency commanded by the probe.

BRIEF DESCRIPTION OF THE DRAWING

The aforementioned aspects and other features of the invention are explained in the following description, taken in connection with the accompanying drawing figures wherein.

Indentically labeled elements appearing in different ones of the figures refer to the same element but may not be referenced in the description for all figures.

DETAILED DESCRIPTION OF THE INVENTION

Figure 1:
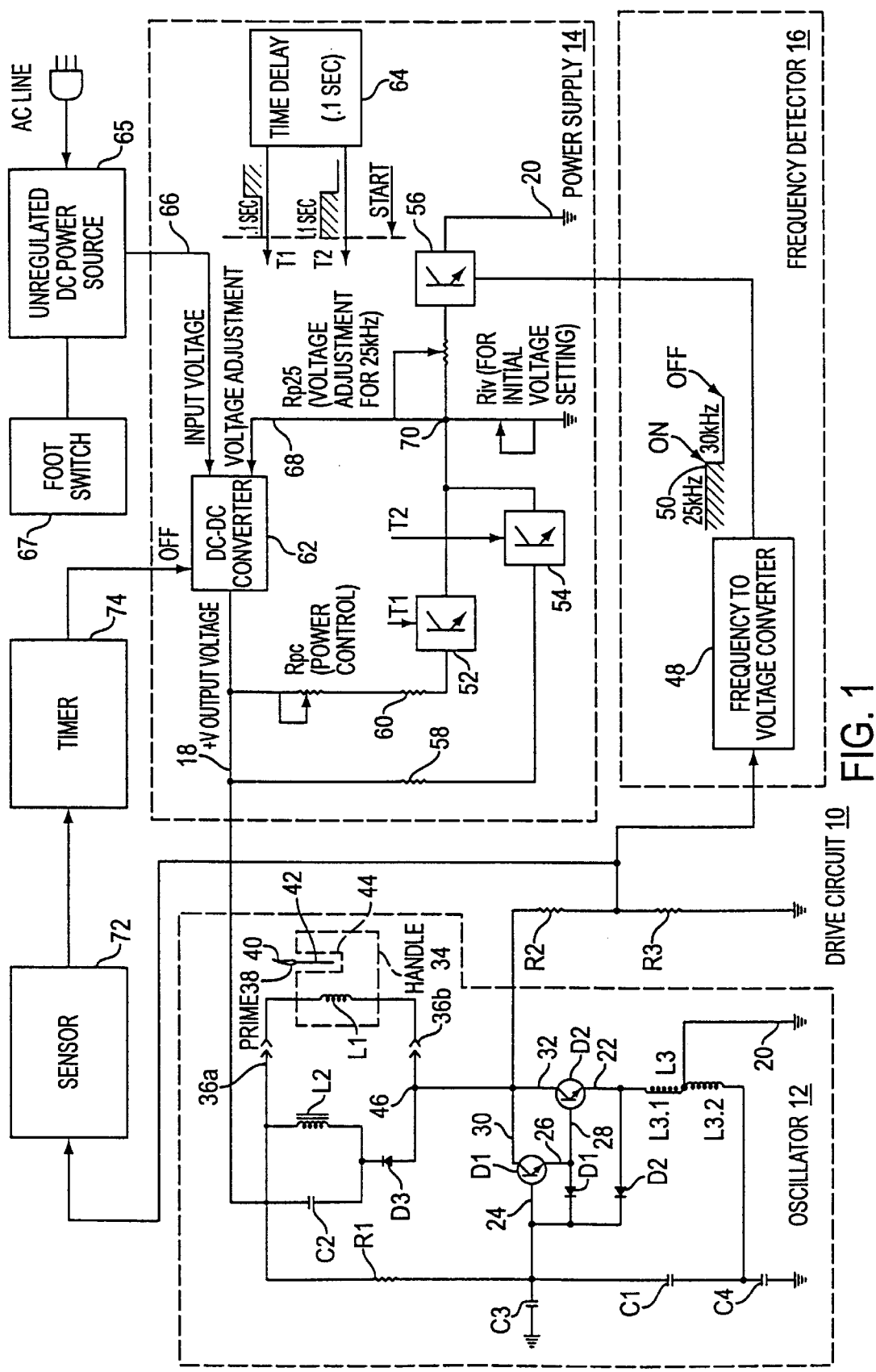
FIG. 1 is an electrical schematic diagram of the drive circuit constructed in accordance with the invention.

FIG. 1 shows a drive circuit 10 comprising an oscillator 12, a power supply 14, a frequency detector 16, a sensor 72 and a timer 74. The power supply 14 outputs power to the oscillator 12 between positive voltage terminal 18 and ground 20. The oscillator 12 comprises two transistors Q1 and Q2, three diodes D1, D2 and D3, handle coil L1, one inductor L2 and one tapped coil L3, four capacitors C1, C2, C3 and C5 and resistor R1. The tapped coil L3 is center tapped to ground. One section, L3.1, of the tapped coil L3 is connected between the emitter 22 of the transistor Q2 and ground, and the second section L3.2 of the tapped coil L3 is connected in series with the capacitor C1 between ground and the base 24 of the transistor Q1.

Resistor R1 connects between the base 24 of transistor Q1 to the terminal 18 of the power supply 14 for supplying base current to the transistor Q1. The emitter 26 of transistor Q1 supplies base current to the base 28 of the transistor Q2, whereby the transistors Q1 and Q2 are connected as a Darlington pair. The diode D1 is connected in back-biased manner between the emitter 26 and the base 24 of the transistor Q1. The diode D2 is connected in back-biased manner between the emitter 22 of the transistor Q2 and the base 24 of the transistor Q1. The handle coil L1 connects the power supply terminal 18 to the collector 30 of the transistor Q1 as well as to the collector 32 of transistor Q2 for application of DC power to the transistors Q1 and Q2. By way of example, the transistors Q1 and Q2 are shown as NPN type transistors.

The handle coil L1 is carried within a handle 34, and is connected to the oscillator 12 via contacts 36 *a* and *b* of an interconnecting electric cord between the handle 34 and the drive circuit 10. The oscillator 12 develops an oscillatory current which flows through the handle coil L1. An insert, constructed as a probe 38 having a vibratory tip 40 connected to a magnetostrictive element 42, is inserted within a compartment 44 of the handle coil. The location of the compartment 44 relative to the handle coil L1 allows for coupling of the magnetic field of the handle coil L1 to the magnetostrictive element 42. Thereby, an oscillating magnetic field produced within the handle coil L1 by the current of the oscillator 12 is coupled into the magnetostrictive element 42 to produce therein vibratory movement which is coupled to the tip 40. The handle coil L1 with the probe 38 serves as a load for the oscillator 12, and extracts power therefrom during operation of the oscillator 12. The electric power outputted by the oscillator 12 is converted to mechanical vibratory power of the probe 38. The insert, or probe 38, is readily extracted from the compartment 44 by a dentist, or other user of the insert, to be replaced by some other insert as may be required to perform a specific task.

In the operation of the oscillator 12, the inductance of the tapped coil section L3.2 resonates with the capacitance of the capacitor C1 in a feedback path which couples alternating current from the emitter circuit of the transistor Q2 to the base 24 of the transistor Q1. This induces oscillation within the oscillator 12. The Darlington pair of the transistors Q1 and Q2 presents a much higher impedance and signal amplification to the feedback path of tapped coil section L3.2 and capacitor C1 than would be provided by either one of the transistors Q1 and Q2 by itself. This increases the effect of gain of the feedback circuit and enlarges the frequency range of oscillation. The diodes D1 and D2 are in a state of nonconduction when the voltage at the base 24 of the transistor Q1 becomes positive relative to the voltage at the emitter 22 of the transistor Q2. Current flows through the diodes D1 and D2 when the voltage at the base 24 of the transistor Q1 becomes negative relative to the voltage at the emitter 22 of the transistor Q1. Therefore, during one portion of an oscillatory cycle of current in the tapped coil L3, current flows through the transistor Q2 while, during reverse flow of current through the tapped coil L3, the a second portion of the oscillatory cycle, the current of the tapped coil L3 flows through the diode D2.

The total of the collector currents of the transistors Q1 and Q2 flows through the handle coil L1. Thereby, the inductance of the handle coil L1 plays a role in the turning of the oscillator 12 to oscillate at a specific oscillation frequency. The inductance of the handle coil L1 and probe 38 is dependent, in part, on the amount of the magnetostrictive material present in the magnetostrictive element 42. Therefore, upon interchange among the inserts, as by exchanging one probe 38 for another probe 38, there is a change in the amount of the magnetostrictive material with a corresponding shift in the oscillation frequency of the oscillator 12. By way of example, it is desirable to employ oscillation frequency of 25 kHz (kilohertz) and 30 kHz. Thus, in accordance with a feature of the invention, this shift in frequency is obtainable by simply interchanging probes.

In order to provide for a circuit wherein oscillatory current of the handle coil L1 is able to flow, thereby to avoid generation of spikes and to absorb other irregularities in the inductor current, the capacitor C2 is connected in parallel to the inductor L2 to form a tank circuit which is connected to terminal 18 and, via the diode D3 to the collector terminals of the transistors Q1 and Q2. The diode D3 is normally back-biased. The capacitance of the capacitor C2 and the inductance of the inductor L2 also produce a resonance which, in combination with the inductance of the handle coil L1 and probe 38 and in combination with the inductance of the tapped coil L3 and the capacitance of the capacitor C1, is operative to establish the frequency of oscillation. The direction of forward conductance in the diode D3 provides a path for the flow of current in the handle coil L1 during such part of the oscillation cycle wherein the transistors Q1 and Q2 are rendered nonconductive.

The foregoing operation of the oscillator 12 provides for energization of the handle coil L1 with alternating current (AC) at the frequency established by the characteristics of a selected probe 38. The operator holds the handle 34 to direct the probe 38 to a desired location wherein work is to be performed.

Figure 2:
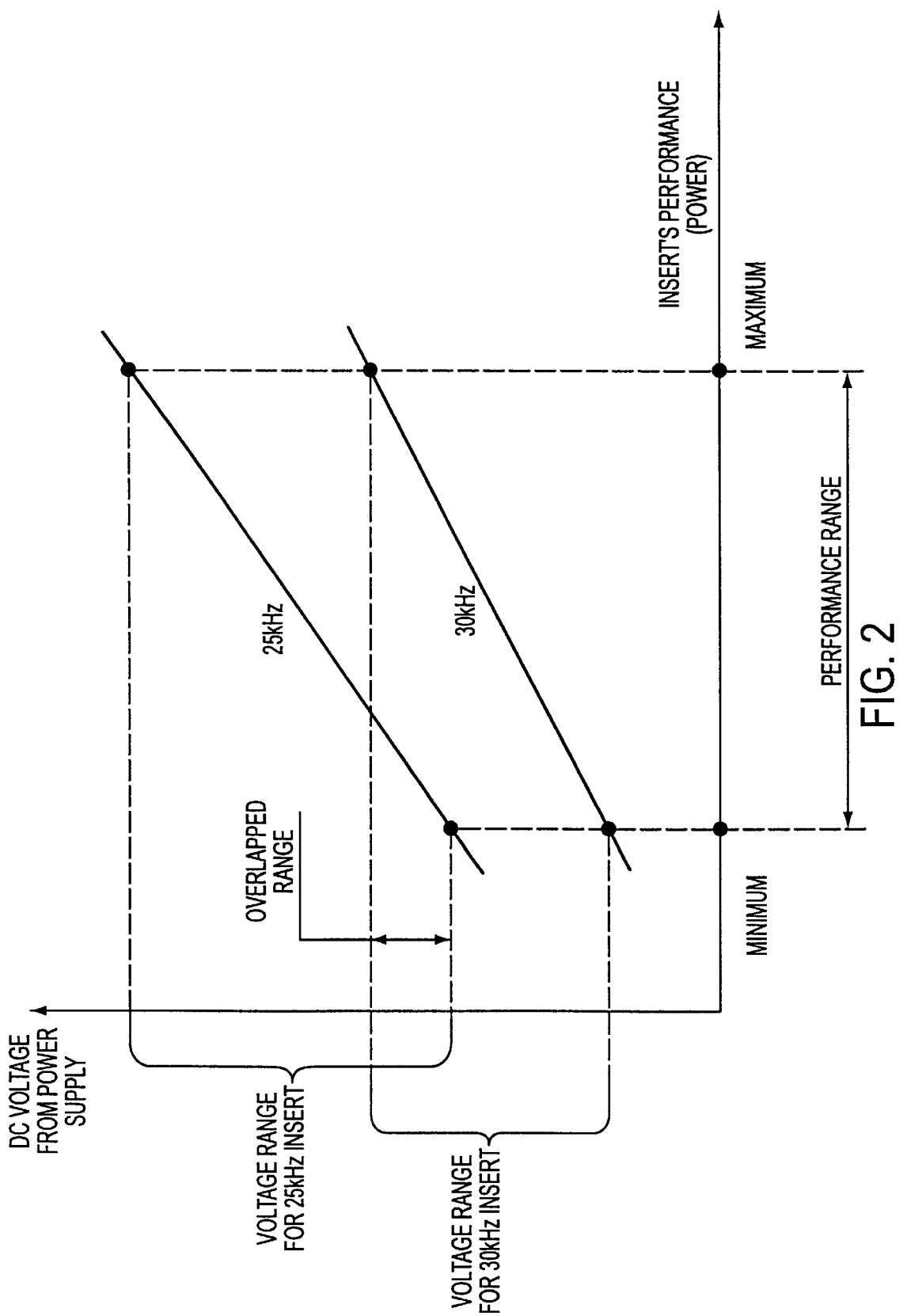
FIG. 2 is a graph showing output voltage of the drive circuit as a function of insert performance for different frequency inserts.

A characteristic of the oscillator 12, as well as of other oscillator circuits of the prior art is depicted in FIG. 2 which shows that the insert's performance depends upon Power Supply 14 voltage. In particular, in the case of oscillator 12, for the same insert's performance Power Supply 14 provides greater output voltage for a 25 kHz insert than for a 30 kHz insert.

In order to insure that the output voltage and performance at 30 kHz is to be the same as the output voltage and performance at 25 kHz, or, generally speaking, may have any desired relationship such as being even greater than the voltage at 25 kHz, the invention provides the feature of employing the frequency detector 16 to control the power supply 14 to provide a desired output supply voltage at terminal 18 as a function of oscillation frequency. This is accomplished in the following manner.

A fraction of the output voltage at the node 46 is obtained via a resistive voltage divider consisting of a series circuit of resistors R2 and R3, and applied to a frequency-to-voltage converter 48 within the frequency detector 16. The converter 48 is operative to convert the oscillation frequency to a voltage level, as is depicted at graph 50. By way of example, as shown in graph 50, a relatively high voltage is indicative of an oscillation frequency of 25 kHz and a relatively low voltage is indicative of an oscillation frequency of 30 kHz. The voltage outputted by the converter 48 serves as a command signal for operation of the power supply 14.

The power supply 14 comprises three electronic gates 52, 54 and 56 which are constructed as transistor gating circuits, and represented in the figure by transistors. Also included in the power supply 14 are two resistors 58 and 60, and three potentiometers Rpc, Rp25 and Riv. Also included in the power supply 14 are a DC—DC converter 62 and a time-delay circuit 64. In the operation of the power supply 14, input voltage from an unregulated power source (shown at 65) is applied via line 66 to the converter 62 in response to operation of a foot switch (67) by the operator. The converter 62 converts the voltage on line 66 to the desired output voltage at terminal 18. An electronic voltage adjustment at line 68 is incorporated into the converter 62 for establishing a desired value of the voltage at terminal 18 in accordance with a value of voltage established at line 68.

To illustrate operation of the power supply 14, the adjustment voltage on line 68 appears at node 70 which connects with two of the potentiometers Rp25 and Riv, the electronic gates 52 and 54, and via the potentiometer Rp25 to the electronic gate 56. For the case of 25 kHz, the converter 48 places the electronic gate 56 in a state of conduction, thereby connecting the potentiometer Rp25 between node 70 and ground 20. Thereby, the two potentiometers Rp25 and Riv are connected in parallel, such that the potentiometer Riv is available for presetting the initial voltage at the node 70, utilizing at 30 kHz probe 38. The potentiometer Rp25 is available for initial adjustment of the voltage outputted by the converter 62 at terminal 18, using a 25 kHz probe 38. In the case of the 30 kHz probe 38, the converter 48 places the electronic gate 56 in a state a noncondition, thereby disconnecting the potentiometer Rp25 so that the output voltage of the converter at terminal 18 is established by the setting of the potentiometer Riv. It is noted also that the voltage appearing at node 70 is obtained also in conjunction with the series connection of the potentiometer Rpc, the resistor 60 and the electronic gate 52 between the terminal 18 and the node 70. In addition, there is a contribution to the voltage at the node 70 by the series connection of the resistor 58 and the electronic gate 54 between the terminal 18 and the node 70.

In accordance with a further feature of the invention, there is provided a manual power adjustment via the potentiometer Rpc which may be located at a point of convenience, such as on a front panel of the electronic assembly of the drive circuit 10. This potentiometer enables the user to increase or decrease voltage online 68 for a corresponding adjustment of voltage at terminal 18. However, in order to insure that the proper voltage is present initially, there is provided an initial delay before the manual control of the potentiometer Rpc becomes effective.

A time delay of approximately 0.1 second is established when the foot switch turns on the drive circuit 10. During this delay, a timing signal T2 is provided by the delay circuit 64 and is applied to the electronic gate 54, thereby placing the electronic gate 54 in a state of conduction. At this time, a timing signal T1, also provided by the delay circuit 64, places the electronic gate 52 in a state of nonconduction. Thus, during this interval of time, the potentiometer Rpc is disconnected from the node 70. However, current flows from terminal 18 via resistor 58 and the potentiometer Riv to establish a desired voltage at the node 70. By way of example, this initial setting of the power supply 14 may provide a specific voltage at terminal 18.

Further, in the operation of the power supply 14, it is noted whether the converter 48 is requesting operation at 25 kHz or at 30 kHz, with a resulting placing of the electronic gate 56 in a state of conduction of nonconduction, as has been described above. Thereby, after the initial delay of approximately 0.1 seconds, the output voltage at terminal 18 has a desired value for operation at either the 25 kHz or 30 kHz. In particular, it is noted that the drive voltage, outputted by the oscillator 12 at node 46, is essentially proportional to the power supply voltage at terminal 18 so that any alteration in the magnitude of the voltage at terminal 18 produces a corresponding change in the magnitude of the voltage at node 46 for driving the handle coil L1 and the probe 38.

Figure 3A:
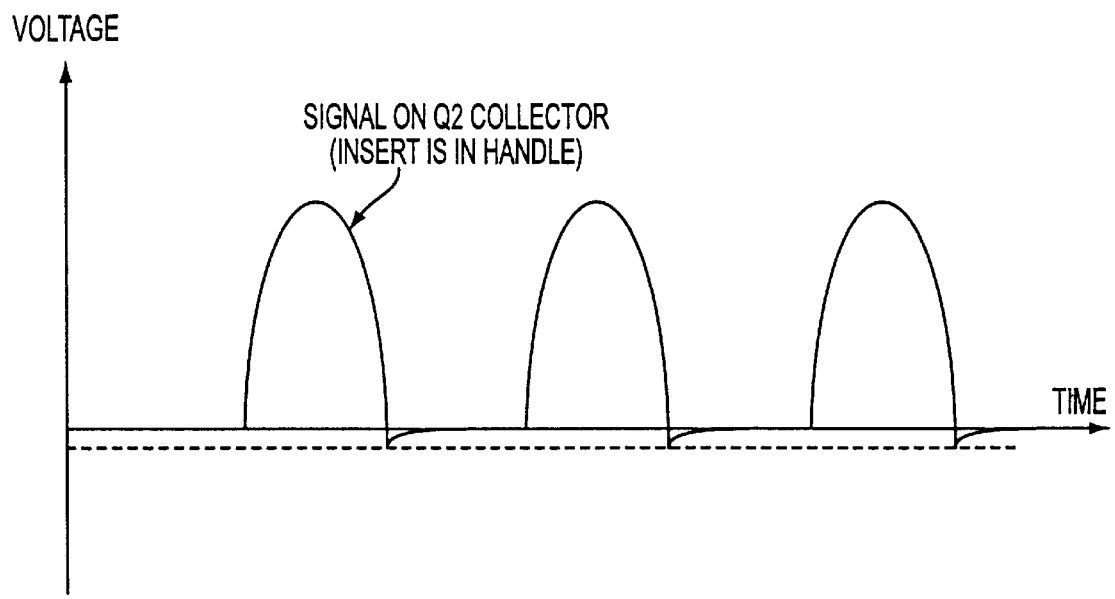
FIGS. 3a and 3b are graphs of waveforms of an output signal of the drive circuit with and without the presence of an insert.
Figure 3B:
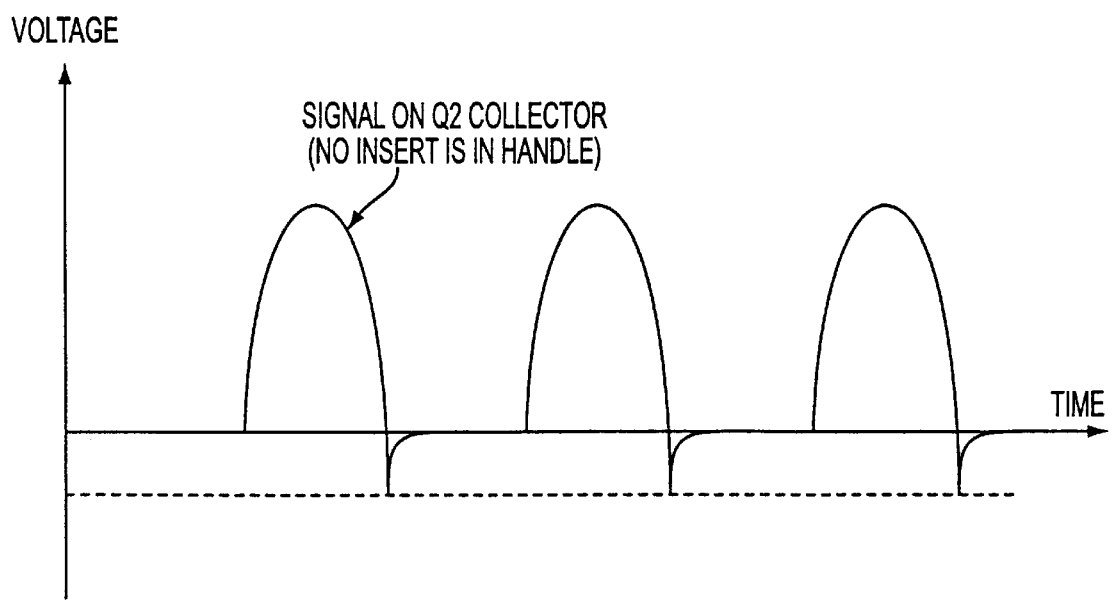

The drive circuit 10 also includes a protective device having an operation which may be understood with reference to FIG. 3a and b. FIG. 3a and b shows the voltage at the node 46. When the insert is present within the handle 34 as shown in FIG. 3a, there is a succession of positive signal pulses which include relatively small negative signal in an amplitude range of typically 0.1 to 0.2 volts. However, removal of the insert alters the balance of the inductances and capacitances of the oscillator 12 resulting in a much increased value of the negative signal, such that the negative signal have magnitudes in the range of, for example, 7 to 8 volts as in FIG. 3b. Capacitors C3 and C4 act as filters to differentiate the amplitude of negative signal to determine the absence or presence of a probe 38.

The drive circuit 10 further comprises a sensor 72 of the value of the negative signal at the node 46, and a timer 74 which is triggered by a signal outputted by the sensor 72. Upon each detection of the occurrence of a large negative signal by the sensor 72, the timer 74 is triggered to produce a delay of two seconds. This is accomplished by outputting a gate signal by the timer 74 having a duration of the aforementioned two seconds, the gate signal being applied to the converter 62. The gate signal is effective to deactivate the power supply 14 during this interval of two seconds. At the conclusion of the gate signal, the power supply 14 is reactivated to energize the oscillator 12. However, the foregoing sequence amends of the large negative signals will react earth in the event that the insert is missing from the handle. Accordingly, the foregoing operational sequence is repeated with a detection of the large negative signal by the sensor 72 and an activation of the timer 74 to deactivate the power supply 14. The procedure is repeated until such time as the insert is replaced into the handle 34. At this time the output voltage at terminal 18 is maintained.

The foregoing feature is advantageous in keeping the power supply 14 in substantially a continuous state of deactivation, other than during the occurrence of minor timer intervals associated with the intermittent negative signals. In practice, this feature enables the user to remove the insert and, in the event that the user fails to turn off the drive circuit 10, the drive circuit 10 effectively turns itself off by not applying power to the handle coil L1 of the handle 34.

It is to be understood that the above described embodiments of the invention are illustrative only, and that modifications thereof may occur to those skilled in the art Accordingly, this invention is not to be regarded as limited to the embodiments disclosed herein, but is to be limited only as defined by the appended claims.

What is claimed is:

1. An automatic drive circuit for driving any one of a plurality of ultrasonic probes, wherein each of the probes comprises a magnetostrictive unit and a vibratory element to be set into vibration by the magnetostrictive unit upon energization of the magnetostrictive unit with an alternating magnetic field, the drive circuit comprising:

an energizing coil enclosed within a handle, the handle having a compartment for receiving one of said probes, the coil being located with the handle adjacent to the compartment for applying the alternating magnetic field to the magnetostrictive unit upon insertion of the probe into the handle and upon an energizing of the coil by the drive circuit;

an oscillator coupled to the coil for applying an oscillatory current to the coil, said coil being connected as a part of an oscillatory circuit of said oscillator enabling inductance of said coil to establish an oscillation frequency of said oscillator, and said compartment serving to position said magnetostrictive unit relative to said coil to establish a value of inductance of said coil; and wherein the magnetostrictive elements of respective probes are operative to establish a plurality of values of inductance for the energizing coil corresponding to separate values of desired vibration frequencies for respective ones of said plurality of probes, thereby to adjust the frequency of oscillation of the oscillator for each of the respective probes.

2. A circuit according to claim 1 wherein there are two of said probes operative respectively at a first frequency, and at a second frequency higher than the first frequency.

3. A circuit according to claim 1 further comprising:

a frequency sensor for sensing a frequency of the oscillatory current, the sensor outputting a signal designating a magnitude of the frequency; and an amplitude control circuit coupled to the oscillator and being respective to the frequency sensor signal for assigning a value of amplitude to the oscillatory current in accordance with a value of the frequency.

4. A circuit according to claim 3, wherein there are two of said probes operative respectively at a first frequency and a second frequency higher than the first frequency, the performance of each of said probes depending upon the amplitude of the oscillatory current in the oscillator and wherein said amplitude means provides the appropriate voltage for each of said probes such that both their performance can be operated at a maximum.

5. A circuit according to claim 1, wherein said oscillator includes a tapped coil in its input circuit for providing feedback to the oscillator.

6. A circuit according to claim 5, wherein said oscillator comprises a Darlington transistor pair for providing signal amplification to the feedback path of the tapped coil thereby enlarging the frequency range of oscillation of the oscillator.

7. An automatic drive circuit for driving any one of a plurality of ultrasonic probes, wherein each of the probes comprises a magnetostrictive unit and a vibratory element to be set into vibration by the magnetostrictive unit upon energization of the magnetostrictive unit with an alternating magnetic field, the drive circuit comprising:

an energizing coil enclosed within a handle, the handle having a compartment for receiving one of said probes, the coil being located with the handle adjacent to the compartment for applying the alternating magnetic field to the magnetostrictive unit upon insertion of the probe into the handle and upon an energizing of the coil by the drive circuit;

an oscillator coupled to the coil for applying an oscillatory current to the coil;

wherein the magnetostrictive elements of respective probes are operative to establish values of inductance for the energizing coil, thereby to adjust the frequency of oscillation of the oscillator for each of the respective probes;

the automatic drive circuit further comprises a frequency sensor for sensing a frequency of the oscillatory current, the sensor outputting a signal designating a magnitude of the frequency;

an amplitude control circuit coupled to the oscillator and being responsive to the frequency sensor signal for assigning a value of amplitude to the oscillatory current in accordance with a value of the frequency; and a power supply for powering said oscillator, wherein said amplitude means comprises a voltage regulation unit within said power supply, and a delay circuit for introducing a delay sequence to the establishment of a voltage outputted by the regulation unit during initial start-up of the drive circuit.

8. A circuit according to claim 7, wherein said voltage regulation unit controls the voltage level of the probes.

9. A circuit according to claim 7, and further comprising a voltage setting circuit operative during said delay for assigning a start up voltage amplitude to the oscillatory circuit suitable for operating across a large frequency range.

10. An automatic drive circuit for driving any one of a plurality of ultrasonic probes, wherein each of the probes comprises a magnetostrictive unit and a vibratory element to be set into vibration by the magnetostrictive unit upon energization of the magnetostrictive unit with an alternating magnetic field, the drive circuit comprising:

an energizing coil enclosed within a handle, the handle having a compartment for receiving one of said probes, the coil being located with the handle adjacent to the compartment for applying the alternating magnetic field to the magnetostrictive unit upon insertion of the probe into the handle and upon an energizing of the coil by the drive circuit;

an oscillator coupled to the coil for applying an oscillatory current to the coil; and wherein the magnetostrictive elements of respective probes are operative to establish values of inductance for the energizing coil, thereby to adjust the frequency of oscillation of the oscillator for each of the respective probes;

the oscillator produces a waveform dependent on the presence of a probe within the handle, the waveform having a characteristic indicative of the absence of the probe from the handle, the circuit further comprising:

a power supply for providing power to said oscillator; and a waveform sensor of said characteristic of the waveform for outputting a signal for deactivating said power supply upon a sensing of said characteristic in said waveform.

11. A circuit according to claim 10 further comprising a timer interconnecting said waveform sensor with said power supply, said timer being responsive to said waveform sensor signal to provide a gating signal of predetermined time duration for deactivating said power supply only during said gating signal, said power supply being reactivated upon termination of said gating signal.

12. An automatic drive circuit for driving an ultrasonic probe wherein the probe comprises a magnetostrictive unit and a vibratory element to be set into vibration by the magnetostrictive unit upon energization of the magnetostrictive unit with an alternating magnetic field, the drive circuit comprising:

a handle having a compartment for receiving said probe;

an oscillator for applying an oscillatory current to the probe, and a sensor for sensing the presence of the probe in the handle and deactivating the power supply when the probe is removed from the handle.

13. A circuit according to claim 12 and further comprising a power supply for providing power to said oscillator, and wherein said sensor is a waveform sensor for sensing the output waveform of the oscillator and wherein the output waveform has characteristics indicative of the absence of the probe from the handle.

14. A circuit according to claim 13 and further comprising a timer interconnecting said waveform sensor with said power supply, said timer being responsive to said waveform sensor signal to provide a gating signal of predetermined time duration for deactivating said power supply only during said gating signal, said power supply being reactivated upon termination of said gating signal.

15. An automatic drive circuit for driving any one of a plurality of ultrasonic probes, wherein each of the probes comprises a magnetostrictive unit and a vibratory element to be set into vibration by the magnetostrictive unit upon energization of the magnetostrictive unit with an alternating magnetic field, the drive circuit comprising:

an oscillator coupled to the coil for applying an oscillatory current to the coil, said coil being connected as a part of an oscillatory circuit of said oscillator enabling inductance of said coil to establish an oscillation frequency of said oscillator, and said compartment serving to position and magnetostrictive unit relative to said coil to establish a value of inductance of said coil; and a power supply for powering said oscillator, said power supply comprising:

a frequency sensor for sensing a frequency of the oscillator current and producing an output signal designating a magnitude of frequency; and an amplitude control circuit coupled to the oscillator and being responsive to the frequency sensor signal for establishing a plurality of values of amplitude to the oscillatory current in accordance with a plurality of values of the frequency.

16. An automatic drive circuit for driving any one of a plurality of ultrasonic probes, wherein each of the probes comprises a magnetostrictive unit and a vibratory element to be set into vibration by the magnetostrictive unit upon energization of the magnetostrictive unit with an alternating magnetic field, the drive circuit comprising:

an oscillator coupled to the coil for applying an oscillatory current to the coil;

a power supply for powering said oscillator, said power supply comprising:

a frequency sensor for sensing a frequency of the oscillator current and producing an output signal designating a magnitude of frequency;

an amplitude control circuit coupled to the oscillator and being responsive to the frequency sensor signal for sending a value of amplitude to the oscillator current in accordance with the value of the frequency; and a voltage regulation unit within said power supply, and a delay circuit for introducing a delay sequence to the establishment of a voltage outputted by the regulation unit during initial start-up of the drive circuit.

17. A circuit according to claim 16 wherein said voltage regulation unit controls the power of the oscillatory current.

18. A circuit according to claim 17 and wherein said delay circuit includes a voltage setting circuit for setting a fixed amplitude on the oscillatory current suitable for a wide range of frequency operation.

* * * * *

UNITED STATES PATENT AND TRADEMARK OFFICE
CERTIFICATE OF CORRECTION

PATENT NO.    : 6,241,520 B1
DATED         : June 5, 2001
INVENTOR(S)   : Igor Y. Gofman et al.

It is certified that error appears in the above-identified patent and that said Letters Patent is hereby corrected as shown below:

<u>Title page,</u>
The Residence of Joseph G. Colombo should read -- Lodi, New Jersey --.

Signed and Sealed this

Twenty-ninth Day of January, 2002

Attest:

*Attesting Officer*

JAMES E. ROGAN
*Director of the United States Patent and Trademark Office*